(12) United States Patent
Maino

(10) Patent No.: US 6,669,473 B1
(45) Date of Patent: Dec. 30, 2003

(54) ANCHOR SCREW FOR ORTHODONTIC TREATMENTS

(75) Inventor: Bortolo Giuliano Maino, Vicenza (IT)

(73) Assignee: Nicos Sas di de Toni Nicoletta & C., Vicenza (IT)

( * ) Notice: Subject to any disclaimer, the term of this patent is extended or adjusted under 35 U.S.C. 154(b) by 34 days.

(21) Appl. No.: 10/130,690

(22) PCT Filed: Nov. 24, 2000

(86) PCT No.: PCT/EP00/11722

§ 371 (c)(1),
(2), (4) Date: May 22, 2002

(87) PCT Pub. No.: WO01/37752

PCT Pub. Date: May 31, 2001

(65) Prior Publication Data (65)

(30) Foreign Application Priority Data

Nov. 26, 1999 (IT) .......................................... V199A0241

(51) Int. Cl.[7] ................................................ A61C 7/00
(52) U.S. Cl. ........................................ 433/18; 433/174
(58) Field of Search ............................... 433/2, 18, 22, 433/174, 173

(56) References Cited

U.S. PATENT DOCUMENTS

| 3,579,831 A | * | 5/1971 | Stevens et al. ............. 433/174 |
| 4,468,200 A | * | 8/1984 | Munch ........................ 433/174 |
| 5,820,369 A |   | 10/1998 | Kvarnström et al. ........... 433/7 |

FOREIGN PATENT DOCUMENTS

| FR | 2681777 | 4/1993 |
| WO | WO 96 12451 | 5/1996 |

* cited by examiner

Primary Examiner—Kevin Shaver
Assistant Examiner—Melba Bumgarner
(74) Attorney, Agent, or Firm—Dykema Gosset PLLC

(57) ABSTRACT

The invention discloses an anchor screw (10) to the palatal vault for orthodontic correction treatments comprising: a lower threaded portion (1) adapted to be screwed to the bone; a substantially cylindrical central portion (2) protruding from the bone and the gum adapted to allow anchorage of traction and/or thrust orthodontic devices; an upper portion (3) provided with movement means (4) to screw and unscrew the screw. The central portion (2) has a reduced diameter zone (6) in comparison with the diameter of the cylindrical portion and at least a hole (5) for the passage of orthodontic devices such as round and/or rectangular/square wires.

8 Claims, 2 Drawing Sheets

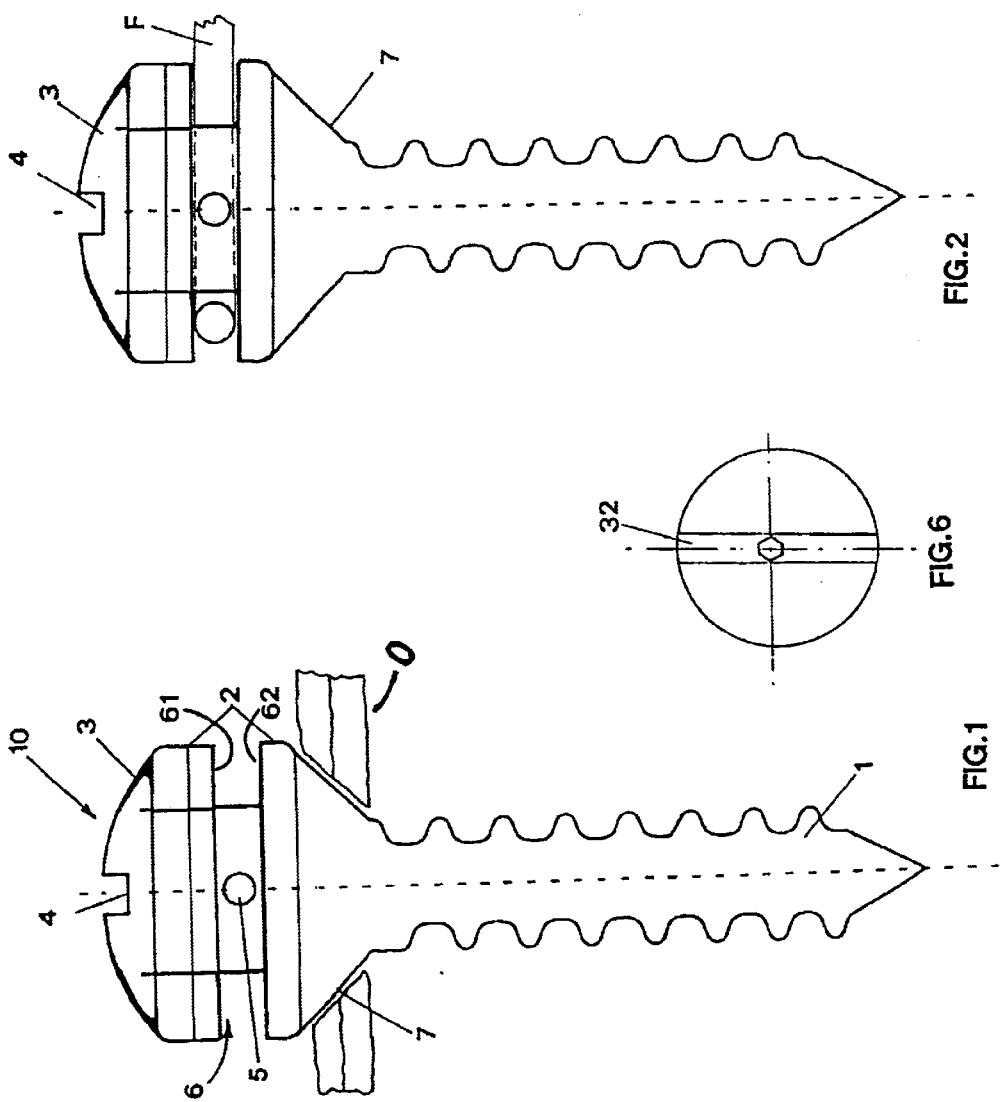

ANCHOR SCREW FOR ORTHODONTIC TREATMENTS

The invention concerns an anchor screw to be applied on the palatal vault or any other part of the mouth, more particularly of mandible and maxilla to anchor devices used in the orthodontic correction.

It is well known that the orthodontic technique provides for the application to the tooth to be treated one or more forces of predetermined strength and the direction in order to correct the attitude for aesthetic reasons or even masticatory function.

The forces are transmitted to the tooth to be treated through orthodontic devices generally consisting of wires, bars or other mechanical traction and/or thrust elements.

These orthodontic devices are generally anchored through auxiliary external devices to anchoring zones outside the mouth or they can be connected to endoosteal implants inside the mouth or tooth screws fixed in the alveolar, palatal, zygomatic bone and so on. These screws have an anchoring function and have a lower threaded portion screwed to the bone, an upper portion provided with movement means to screw and unscrew said screw in the alveolar, palatal arch and so on and a central portion protruding from the gum to which said orthodontic devices are anchored.

More particularly the central portion of the known orthodontic screws is substantially cylindrical and allows to the orthodontic devices such as wires, to be wound perimetrically.

The known technique provides that the orthodontic correction devices are fixed to the above mentioned anchor screws simply rolling up a wire end for instance in the central cylindrical portion of said screw so as to warrant the static stability required to develop the traction or thrust forces adapted to bring the treated tooth in the correct position.

The main drawback is due to the poor-friction created between the orthodontic devices (wire) and the central portion of said screw, therefore the little friction required to with stand the traction and/or thrust forces.

A further drawback is also due to the difficulty to control when applying the orthodontic devices, the traction and/or thrust applied to said tooth, this difficulty arising from the fact of rolling up the wire on the central portion of the anchor screw.

Another drawback is due to the increase of the size of the anchor screw because of the wire rolled up around the central portion. WO 96 12451 A discloses an anchor screw for orthodontic correction treatments in which the anchorage of the orthodontic traction and/or trust devices is permitted by the cooperation of a cylindrical central portion of the screw with a cap superimposed at the end of said screw. FR-A-2681777 discloses and anchor element for orthodontic correction having an upper portion adapted to allow the anchorage of orthodontic traction and/or trust devices.

Other types of screws intended for the same object have shaped heads with grooves in which the terminal parts of the wires of the orthodontic devices may be fixed. A cap threaded on the screw head fixedly blocking the orthodontic wires is also provided.

Such a screw has the drawback of a high cost and also a considerable bulk in the mouth, as well as poor practicality because some zones of the mouth are hardly accessible.

It is an object of the present invention to overcome said drawbacks.

More particularly a first object of the invention is to create an anchor screw that can be applied wherever there is an available bone, allowing a better control of the traction and/or thrust force applied to the tooth to be treated.

Another object is to provide an anchor screw allowing to diminish the bulk of the entire orthodontic system.

A further object is to create a screw with such as shape to allow a better efficiency for the cleaning interventions carried out by patient and required to avoid possible infections.

Last but not least object is to provide an orthodontic screw which is cost effective also in respect of the available performances.

Said objects are obtained by an anchor screw for orthodontic correction treatments the main features of which are according to claim 1.

Advantageously the invention allows a fine regulation also of the direction of the traction and/or thrust force applied on each tooth to be treated.

Furthermore the invention reduces the tedious feeling of the patient due to the presence of foreign elements inside the mouth.

A further advantage of the invention is to allow to anchor more orthodontic devices at the same time.

According to a preferred embodiment of the invention the zone with reduced diameter has a transverse hole in respect of the screw axis suitable for passage of wires or other orthodontic devices so as to improve the anchoring efficiency of said devices, and an easier connection between screw and wire as well.

Further objects and advantages will be better apparent with the description of a preferred embodiment of the invention given as an illustrative but non-limiting example only and illustrated in the accompanying sheets of drawing in which:

FIG. 1 shows the anchor screw according to the invention;

FIG. 2 is a side view of the screw of FIG. 1;

FIGS. 5 and 6 show another variation of the upper portion of the screw of the invention.

Figure 5:
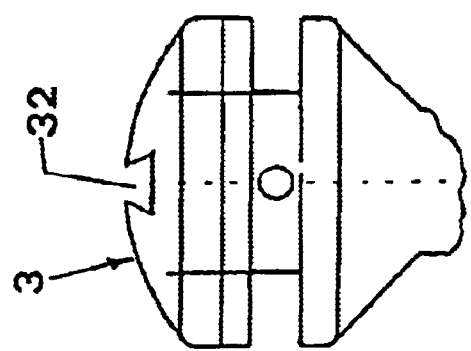

The bone anchoring screw for orthodontic correction treatments of the present invention is shown in FIG. 1 where it is generally indicated with reference numeral 10.

In the screw one can see a lower threaded portion 1 adapted to be screwed in the bone O, a central portion 2 protruding from bone O and an upper portion 3 provided with movement means 4 to screw and unscrew said lower portion 1 to the bone structure O.

In the central portion 2 there is a zone 6 with reduced diameter suitable for passage and fastening of a traction or thrust member such as a wire F. The reduced zone 6 is actually an annular space of rectangular or square section but not curved for the reasons that will be explained hereinafter.

In the transversal narrowing 6 in the case of the embodiment of FIG. 1 there are two diametral through holes 5 at right angles to one another for the passage of wire or orthodontic devices that are then anchored being bent on the groove 6.

The fact that the reduced zone or groove 6 is willingly made with surfaces 61 and 62 in a flat radius, depends from the fact that this groove may have the function of antirotational devices for the orthodontic device in the event that the cross section of said device is not round. Indeed in some orthodontic applications it is necessary that the orthodontic device does not undergo any rotation during its application. This is clearly prevented by the configuration of the reduced zone and more particularly the non round configuration, that is when the surfaces 61 and 62 are flat and parallel to one another.

Another feature of the invention can be seen in FIG. 1 where between the lower threaded portion 1 and the central portion 2 there is a conical zone 7 connecting said threaded portion and the central portion. The taper of the zone is functional because in view of this taper it is very easy to clean the mouth, for instance by a conventional tooth brush, around the screw emerging portion which is close to the soft tissues. This allows a better hygienic control and prevents formation of local infections due to food deposited between the gum and the screw.

As to the movement means 4, in the illustrated embodiment they consist of a star shaped recess adapted to receive a corresponding tool such as a screw driver to thread the anchor screw 10 to the palatal vault.

Figure 3:
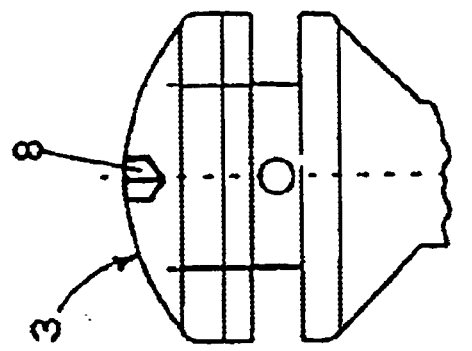
FIG. 3 shows a variation of the movement means for the upper portion of the screw of the invention.

Alternatively the movement means 4 consists of a simple cut for a screw driver or a recessed head 8 for the movement with a tool adapted to move socket head screws as shown in FIG. 3.

In connection with the upper portion 3, it has a curved contour allowing to match the curved shape of some teeth such as for instance the premolars.

Figure 4:
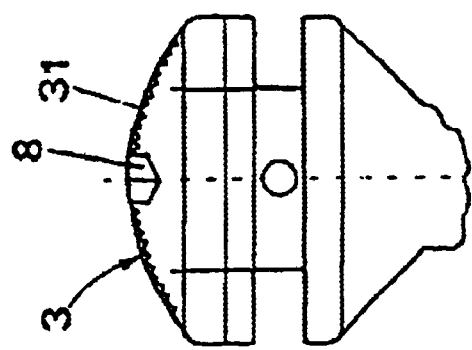
FIG. 4 shows a variation of the upper portion of the screw of the invention.

According to a variation of the invention the head 3 having a generally curved contour, has a rather protruding textured surface 31 as seen in FIG. 4, for the purpose of applying to the head further orthodontic devices such as tubes, brackets or other directly adhesive devices.

According to another variation shown in FIGS. 5 and 6, the screw head 3 has a continuous undercut groove 32 so as to make easier anchorage of further orthodontic devices that would be required to be applied to the screw head with direct stick.

In operation firstly the anchor screw will be fixed to the bone using the proper tool. Once the orthodontic devices constituting the traction and or thrust elements, consisting for instance of a metal wire F are applied, the metal wire will be inserted in the corresponding through hole 6 made in the central portion 3 of the anchor screw. Then the required force will be applied to the metal wire stretching it to bend the wire on the groove 6 so as to obtain anchorage and application of the desired traction and/or thrust force as shown in FIG. 2, and protecting the soft tissues from the wire cut end.

Finally by acting on the movement means 4, it is possible to address and change the direction of application of the traction and/or thrust force, increasing or decreasing its amount by simply rotating the anchor screw 1 and therefore the direction of the axis of the through hole 6.

It is to be noted that the joint action of wire and through hole 6 and wire curve, warrants the required tightness and this allows to avoid to roll up the wire around the central portion 3 of the screw 1.

Although the invention was described with reference to the accompanying drawings, it may be subject to constructional modifications falling in the appended claims and therefore covered by the present invention.

What is claimed is:

1. An anchor screw having a central axis, said screw for securing orthodontic correction treatments comprising:

a lower threaded portion adapted to be screwed into a bone;

a substantially cylindrical central portion having an outer diameter, said central portion protruding from said bone and gum when the lower threaded portion is screwed into the bone, and being adapted to allow anchorage of orthodontic devices thereto;

an upper portion provided with movement means to screw and unscrew said screw;

wherein said central portion has a reduced diameter zone in comparison with the outer diameter of said central portion, said reduced diameter zone having flat and parallel surfaces so as to prevent rotation of orthodontic devices, and having at least one opening transverse to the axis of the screw suitable for passage of wires or orthodontic devices.

2. The screw according to claim 1 wherein the opening is in the form of two holes disposed at right angles to one another and transverse to the screw axis.

3. The screw according to claim 1, wherein said lower portion is connected to said central portion through a connecting surface with conical contour.

4. The screw according to claim 1, wherein said upper potion has a curved contour.

5. The screw according to claim 1 wherein said movement means comprises at least one notch transverse to the central axis of the screw.

6. The screw according to claim 1, wherein said movement means comprises a polygonal hole.

7. The screw according to claim 1, wherein said upper portion has a textured surfaces.

8. The screw according to claim 1, wherein said upper portion has a longitudinal groove with an undercut section for allowing anchorage of further orthodontic devices.

* * * * *